United States Patent
Jarrett et al.

(10) Patent No.: US 12,039,462 B2
(45) Date of Patent: *Jul. 16, 2024

(54) COMPUTERIZED SYSTEM AND METHOD OF OPEN ACCOUNT PROCESSING

(71) Applicant: Crowe LLP, Oak Brook, IL (US)

(72) Inventors: Kevin Jarrett, Ridgefield, CT (US);
Eric Boggs, Brentwood, TN (US);
Cory Herendeen, Carmel, IN (US);
Justin Bass, Chicago, IL (US)

(73) Assignee: Crowe LLP, Oak Brook, IL (US)

( * ) Notice: Subject to any disclaimer, the term of this patent is extended or adjusted under 35 U.S.C. 154(b) by 483 days.

This patent is subject to a terminal disclaimer.

(21) Appl. No.: 17/328,065

(22) Filed: May 24, 2021

(65) Prior Publication Data

US 2021/0279612 A1    Sep. 9, 2021

Related U.S. Application Data

(63) Continuation of application No. 15/450,419, filed on Mar. 6, 2017, now Pat. No. 11,062,214.

(60) Provisional application No. 62/304,634, filed on Mar. 7, 2016.

(51) Int. Cl.
| | | |
|---|---|---|
| *G16H 50/70* | (2018.01) | |
| *G06N 3/042* | (2023.01) | |
| *G06N 5/04* | (2023.01) | |
| *G06N 7/01* | (2023.01) | |
| *G06N 20/00* | (2019.01) | |
| *G16H 40/20* | (2018.01) | |

(52) U.S. Cl.
CPC ............... *G06N 5/04* (2013.01); *G06N 3/042* (2023.01); *G06N 7/01* (2023.01); *G06N 20/00* (2019.01); *G16H 40/20* (2018.01); *G16H 50/70* (2018.01)

(58) Field of Classification Search
CPC .......... G16H 50/70; G16H 10/60; G06N 5/04; G06N 3/09; G06Q 40/08
See application file for complete search history.

(56) References Cited

U.S. PATENT DOCUMENTS

| | | | | |
|---|---|---|---|---|
| 2005/0137912 A1* | 6/2005 | Rao | ........................ | G06Q 40/08 |
| | | | | 705/4 |
| 2011/0246262 A1* | 10/2011 | Pepper | .................... | G06Q 40/12 |
| | | | | 706/54 |
| 2015/0081324 A1 | 3/2015 | Adjaoute | | |

(Continued)

OTHER PUBLICATIONS

Canada Examination Report, Subsection 86(2), dated Dec. 1, 2022, CA Application No. 3,016,069, Computerized System and Method of Open Account Processing.

(Continued)

*Primary Examiner* — Mark Holcomb
(74) *Attorney, Agent, or Firm* — Barnes & Thornburg LLP

(57) ABSTRACT

A computerized system and method for health care facilities to reduce manual handling of at least some open account issues. The system provides healthcare facilities with the ability to resolve current open patient account issues by utilizing the data patterns from a facility's historical patient account transaction activity, to create a machine learning model that can predict resolutions to the open accounts. These patterns are then applied to a facility's current transaction data providing next step resolution to each patient account.

17 Claims, 11 Drawing Sheets

(56) References Cited

U.S. PATENT DOCUMENTS

2015/0254555 A1\* 9/2015 Williams, Jr. ......... G06N 3/045
　　　　　　　　　　　　　　　　　　　　706/14

OTHER PUBLICATIONS

New Zealand Examination Report 1, dated Feb. 8, 2023, NZ Application No. 745641, Computerized System and Method of Open Account Processing.

\* cited by examiner

| Posting Date ID | Transaction Description | Transaction Type | Transaction Amount | Account Balance | Total Charges | Vars $x_i,x_p$ |
|---|---|---|---|---|---|---|
| 5/12/2013 | SELF PAY PAYMENT | PAYMENT | (30.00) | 263.00 | 293.00 | ... |
| 7/19/2013 | AETNA TRSCARE ADJ | CONTRACTUAL | (171.96) | 91.04 | 293.00 | ... |
| 7/19/2013 | AETNA TRSCARE PAYMENT | PAYMENT | (102.04) | (11.00) | 293.00 | ... |
| 7/24/2013 | REFUND PATIENT PAYMENT | PAYMENT | 11.00 | 0.00 | 293.00 | ... |

FIG. 9

| TxT 1 | TxT 2 | TxT 3 | TxT 4 | TxA 1 | TxA 2 | TxA 3 | TxA 4 | Total Charges | Vars $x_i,x_p$ | Resolution |
|---|---|---|---|---|---|---|---|---|---|---|
| PAY | CX | PAY | NA | (30.00) | (171.96) | (102.04) | NA | 293.00 | ... | PSP |

FIG. 10

| TxT 1 | TxT 2 | TxT 3 | TxT 4 | TxA 1 | TxA 2 | TxA 3 | TxA 4 | Total Charges | Vars $x_i,x_p$ | Resolution |
|---|---|---|---|---|---|---|---|---|---|---|
| PAY | CX | PAY | NA | (30.00) | (171.96) | (102.04) | NA | 293.00 | ... | PSP |
| PAY | PAY | CX | PAY | (100.00) | (12.00) | (89.11) | (212.91) | 490.02 | ... | ? |

FIG. 11

| Obs | \multicolumn{4}{c}{Used in Iteration i?} | |
|---|---|---|---|---|---|
| | 1 | 2 | 3 | ... | k |
| 1 | 1 | 1 | 3 | | 0 |
| 2 | 1 | 0 | 0 | | 1 |
| 3 | 0 | 1 | 1 | | 0 |
| ... | ... | ... | ... | ... | ... |
| n | 0 | 1 | 1 | | 1 |
| score | .438 | .859 | .1234 | | .833 |

*FIG. 13*

| AccountID | Prediction | Prediction Probability | Original Prediction |
|---|---|---|---|
| 01021134 | 1 | 0.946 | 1 |
| 23214323 | 79 | 0.910 | 79 |
| 32498501 | 3 | 0.99 | 3 |
| 00139281 | 999999 | 0.891 | 3 |

*FIG. 16*

COMPUTERIZED SYSTEM AND METHOD OF OPEN ACCOUNT PROCESSING

RELATED APPLICATIONS

This is a continuation of U.S. patent application Ser. No. 15/450,419 for a "Computerized System and Method of Open Account Processing" filed Mar. 6, 2017, which claimed the benefit of U.S. Provisional Application Ser. No. 62/304,634 filed Mar. 7, 2016, for a "Computerized System and Method of Open Account Processing," which are both hereby incorporated by reference in their entireties.

TECHNICAL FIELD

This disclosure relates generally to computer systems and methods for processing open accounts for healthcare facilities; in particular, this disclosure relates to a computerized system and method that uses machine learning algorithms to analyze prior transaction data to predict, among other things, possible resolutions to open account issues.

BACKGROUND AND SUMMARY

Healthcare facilities manage account transactions to identify exceptions, such as credit balances, claim denials, small balances and underpayments. Although account exceptions often represent only approximately 15% of a healthcare facility's accounts, dealing with these exceptions can be difficult and time consuming. Typically, these accounts are processed in a manual fashion (or handed to a third party vendor) once identified. However, this results in numerous challenges, such as staffing issues, finding the expertise in processing accounts (internally or finding a third party) and/or timeliness in resolving open account issues.

This disclosure relates to a computerized system and method for health care facilities to reduce manual handling of at least some open account issues. In some embodiments, the system provides healthcare facilities with the ability to resolve current open patient account issues by utilizing the data patterns from a facility's historical patient account transaction activity, to create a machine learning model that can predict resolutions to the open accounts. These patterns are then applied to a facility's current transaction data providing next step resolution to each patient account. Additional data intellegence is created as accounts provided with original facility data errors can be identified and corrected account solutions can be added to the machine learning component and then reapplied to the facility's transaction data.

According to one aspect, this disclosure provides an apparatus with a storage device and at least one processor coupled to the storage device. The storage device stores a program for controlling the at least one processor. When the at least one processor operates the program, the processor is configured to obtain training data representative of historical account transactions between a plurality of patients and a healthcare facility. The processor analyzes the training data to create a model configured to make predictions representative of resolutions of open account transactions. The model makes predictions based on one or more current open accounts and data represented by these predictions are transmitted.

Additional features and advantages of the invention will become apparent to those skilled in the art upon consideration of the following detailed description of the illustrated embodiment exemplifying the best mode of carrying out the invention as presently perceived. It is intended that all such additional features and advantages be included within this description and be within the scope of the invention.

BRIEF DESCRIPTION OF THE DRAWINGS

The present disclosure will be described hereafter with reference to the attached drawings which are given as non-limiting examples only, in which:

FIG. 7 is a simplified block diagraph illustrating an ExR system according to one embodiment;

FIGS. 8-11 are tables illustrating preprocessing of data for the ExR system according to one embodiment;

FIG. 13 is a table illustrating example predictions by the machine learning environment according to one embodiment;

FIG. 16 is a table showing example confidence threshold outputs according to one embodiment.

Figure 1:
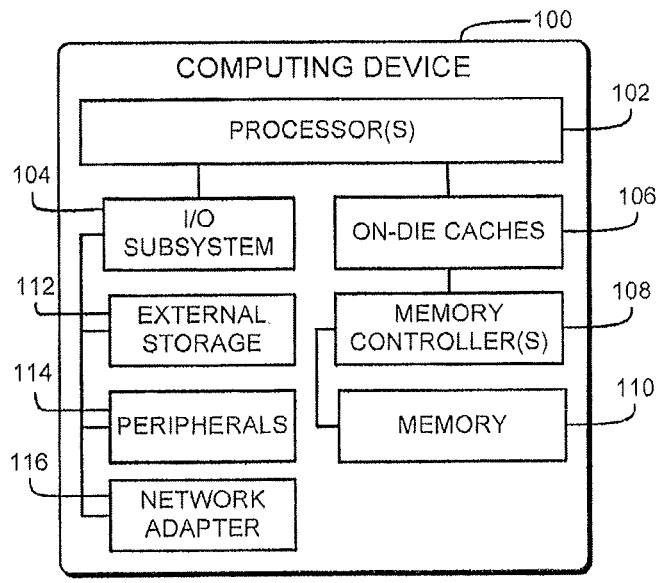
FIG. 1 is a diagrammatic view of an example computing device on which the ExR system could operate according to one embodiment.

Corresponding reference characters indicate corresponding parts throughout the several views. The components in the figures are not necessarily to scale, emphasis instead being placed upon illustrating the principals of the invention. The exemplification set out herein illustrates embodiments of the invention, and such exemplification is not to be construed as limiting the scope of the invention in any manner.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

This disclosure relates generally to a computer system and method for processing open accounts, which will be referred to as the ExR system. The ExR system provides healthcare facilities with the ability to resolve current open patient account issues by utilizing the data patterns from a facility's historical patient account transaction activity, to create a machine learning model. These patterns are then applied to a facility's current transaction data providing next step resolution to each patient account. Additional data intellegence is created as accounts provided with original facility data errors can be identified and corrected account solutions can be added to the "machine learning" component and then reapplied to the facility transaction data. The system will be applicable to all open accounts within a healthcare facility. The facility will supply initial patient account data for the application and through the combination of "themes" and "machine learning" the system provides the facility with the resolution to the open account issue. The term "health care facility" is broadly intended to include any organization or entity that provides health care services, including but not limited to hospitals, clinics, doctors' offices, medical research laboratories, pharmacies, and other healthcare organizations, whether that entity is a for-profit, a non-profit or a governmental facility.

The detailed description which follows is presented in part in terms of algorithms and symbolic representations of operations on data bits within a computer memory representing alphanumeric characters or other information. An algorithm is provided by this disclosure and is generally conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as bits, values, symbols, characters, display data, terms, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements which impart or manifest a physical organization on the information stored in memory. More than mere abstraction, the data structures are specific electrical or magnetic structural elements in memory which simultaneously represent complex data accurately, often data modeling physical characteristics of related items, and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein which form part of the present invention; the operations are machine operations. Useful machines for performing the operations of the present invention include general purpose digital computers or other similar devices. In all cases the distinction between the method operations in operating a computer and the method of computation itself should be recognized. A method and apparatus are disclosed for operating a computer in processing electrical or other (e.g., mechanical, chemical) physical signals to generate other desired physical manifestations or signals. The computer operates on software modules, which are collections of signals stored on a media that represents a series of machine instructions that enable the computer processor to perform the machine instructions that implement the algorithmic steps. Such machine instructions may be the actual computer code the processor interprets to implement the instructions, or alternatively may be a higher level coding of the instructions that is interpreted to obtain the actual computer code. The software module may also include a hardware component, wherein some aspects of the algorithm are performed by the circuitry itself, rather as a result of an instruction.

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

An apparatus is disclosed for performing these operations. This apparatus may be specifically constructed for the required purposes, or it may comprise a general purpose computer as selectively activated or reconfigured by a computer program stored in the computer. The algorithms presented herein are not inherently related to any particular computer or other apparatus unless explicitly indicated as requiring particular hardware. In some cases, the computer programs may communicate or relate to other programs or equipment through signals configured to particular protocols which may or may not require specific hardware or programming to interact. In particular, various general purpose machines may be used with programs written in accordance with the teachings herein, or it may prove more convenient to construct more specialized apparatus to perform the required method steps. The required structure for a variety of these machines will appear from the description below.

In the following description several terms which are used frequently have specialized meanings in the present context. The term "network" means two or more computers which are connected in such a manner that messages may be transmitted between the computers. In such computer networks, typically one or more computers operate as a "server," a computer with large storage devices such as hard disk drives and communication hardware to operate peripheral devices such as printers or modems. The term "browser" refers to a program which is not necessarily apparent to the user, but which is responsible for transmitting messages between the user's computer and the network server and for displaying and interacting with network resources.

Browsers are designed to utilize a communications protocol for transmission of text and graphic information over a worldwide network of computers, namely the "World Wide Web" or simply the "Web." Examples of browsers compatible with the present invention include the Internet Explorer browser program offered by Microsoft Corporation (Internet Explorer is a trademark of Microsoft Corporation), the Chrome browser program offered by Google Inc. (Chrome is a trademark of Google Inc.), the Safari browser program offered by Apple Inc. (Safari is a trademark of Apple Inc.) or the Firefox browser program distributed by the Mozilla Foundation (Firefox is a registered trademark of the Mozilla Foundation). The browser could operate on a desktop operating system, such as Windows by Microsoft Corporation (Windows is a trademark of Microsoft Corporation) or OS X by Apple Inc. (OS X is a trademark of Apple Inc.). In some cases, the browser could operate on mobile operating systems, such as iOS by Apple Inc. (iOS is a trademark of Apple Inc.) or Android by Google Inc. (Android is a trademark of Google Inc.). Browsers display information which is formatted in a Standard Generalized Markup Language ("SGML") or a Hyper Text Markup Language ("HTML"), both being scripting languages which embed non-visual codes in a text document through the use of special ASCII text codes. Files in these formats may be easily transmitted across computer networks, including global information networks like the Internet, and allow the browsers to display text, images, and play audio and video recordings.

Referring now to FIG. 1, an illustrative computing device 100 for executing the exceptions resolutions ("ExR") system, includes at least one processor 102, an I/O subsystem 104, at least one on-die cache 106, and a memory controller 108 to control a memory 110. The computing device 100 may be embodied as any type of device capable of performing the functions described herein. For example, the computing device 100 may be embodied as, without limitation, a computer, a workstation, a server computer, a laptop computer, a notebook computer, a tablet computer, a smartphone, a mobile computing device, a desktop computer, a distributed computing system, a multiprocessor system, a consumer electronic device, a smart appliance, and/or any other computing device capable of analyzing software code segments.

As shown in FIG. 1, the illustrative computing device 100 includes the processor 102, the I/O subsystem 104, the on-die cache 106, and the memory controller 108 to control a memory 110. Of course, the computing device 100 may include other or additional components, such as those commonly found in a workstation (e.g., various input/output devices), in other embodiments. For example, the computing device 100 may include an external storage 112, peripherals 114, and/or a network adapter 116. Additionally, in some embodiments, one or more of the illustrative components may be incorporated in, or otherwise form a portion of, another component. For example, the memory 110 or portions thereof, may be incorporated in the processor 102 in some embodiments.

The processor 102 may be embodied as any type of processor capable of performing the functions described herein. For example, the processor may be embodied as a single or multi-core processor(s), digital signal processor, microcontroller, or other processor or processing/controlling circuit. The memory 110 may be embodied as any type of volatile memory and/or persistent memory capable of performing the functions described herein. In operation, the memory 110 may store various data and software used during operation of the computing device 100 such as operating systems, applications, programs, libraries, and drivers. The memory 110 is communicatively coupled to the processor 102 via the memory bus using memory controller(s) 108, which may be embodied as circuitry and/or components to facilitate input/output operations with the processor 102, the memory 110, and other components of the computing device 100.

The I/O subsystem 104 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 104 may form a portion of a system-on-a-chip (SoC) and be incorporated, along with the processor 102, the memory 110, and other components of the computing device 100, on a single integrated circuit chip.

An external storage device 112 is coupled to the processor 102 with the I/O subsystem 104. The external storage device 112 may be embodied as any type of device or devices configured for short-term or long-term storage of data such as, for example, memory devices and circuits, memory cards, hard disk drives, solid-state drives, or other data storage devices.

The computing device 100 may include peripherals 114. The peripherals 114 may include any number of additional input/output devices, interface devices, and/or other peripheral devices. By way of example only, a peripheral may be a display that could be embodied as any type of display capable of displaying digital information such as a liquid crystal display (LCD), a light emitting diode (LED), a plasma display, a cathode ray tube (CRT), or other type of display device.

Figure 2:
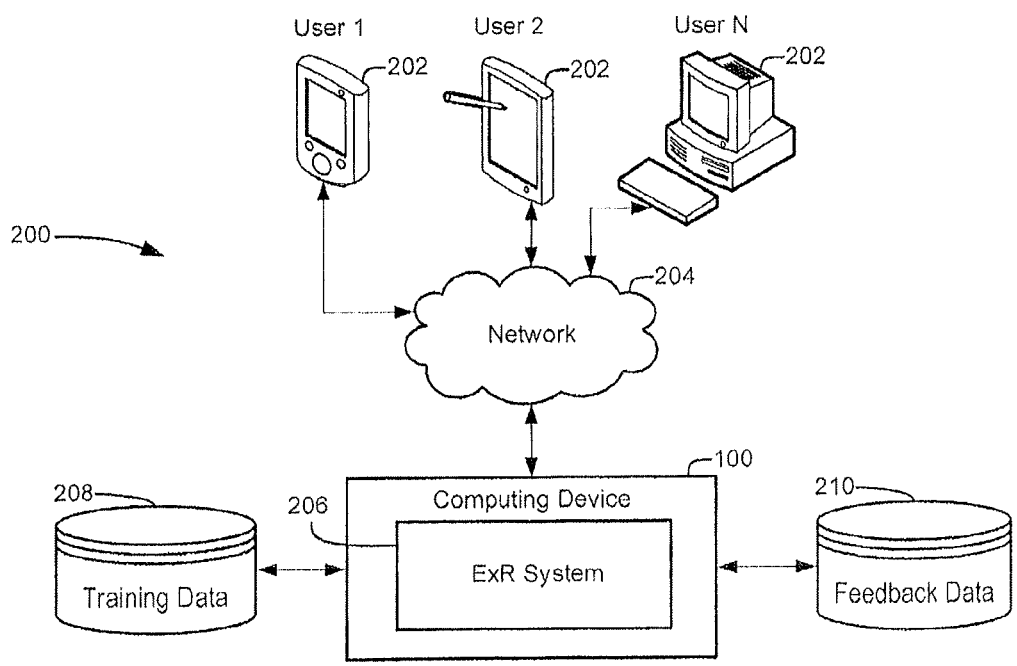
FIG. 2 is a diagrammatic view of an example computing environment in which the ExR system could operate according to one embodiment.

The computing device 100 illustratively includes a network adapter 116, which may be embodied as any communication circuit, device, or collection thereof, capable of enabling communications between the computing device 100 and other remote devices over a computer network (FIG. 2). The network adapter 116 may be configured to use any one or more communication technology (e.g., wired or wireless communications) and associated protocols (e.g., Ethernet, Bluetooth®, Wi-Fi®, WiMAX, etc.) to effect such communication.

FIG. 2 is a high-level block diagram of a computing environment 200 under which the computing device 100 could operate according to one embodiment. FIG. 2 illustrates the computing device 100 and three clients 202 connected by a network 204. Only three clients 202 are shown in FIG. 2 in order to simplify and clarify the description. Likewise, a single computing device 100 is shown for purposes of simplicity, but multiple computing devices could be used. Embodiments of the computing environment 200 may have thousands or millions of clients 202 connected to the network 204, for example, the Internet. Users (not shown) may operate software, such as a browser, on clients 202 to both send and receive messages over network 204 via computing device 100 and its associated communications equipment and software (not shown). For example, the ExR system 206 could be accessed via the computing device 100 using a browser. For example, the ExR system 206 could include a web interface for users to access certain functions of the system. Typically, clients 202 would be able to access the ExR system 206 over the network 204 by entering a web address, such as an IP address, URL, or domain name (web address generally referred to as a "Destination") into browser software. In some embodiments, clients 202 could include a dedicated application that connects with the ExR system 206 instead of using a web browser, such as with an iOS™ app or an Android™ app.

The example in FIG. 2 shows training data 208 and feedback data 210 to which the ExR system 206 has access. The training data 208 includes historical transaction data, such as two years of historical data from an entity, that is used to create a model for making predictions concerning exceptions and the feedback data 210 is a stream of current transactional data that is used to continually improve modeling of the machine learning module discussed below. At a high level, the data may come from patient accounting systems along with EDI 837 and 835 healthcare bills and claim files. Example fields that could be included in the training data 208 and the feedback data 210 include transaction amounts and types, overall account balance, etc. Additional fields are calculated, such as days between transactions, transaction percent, etc.

Figure 3:
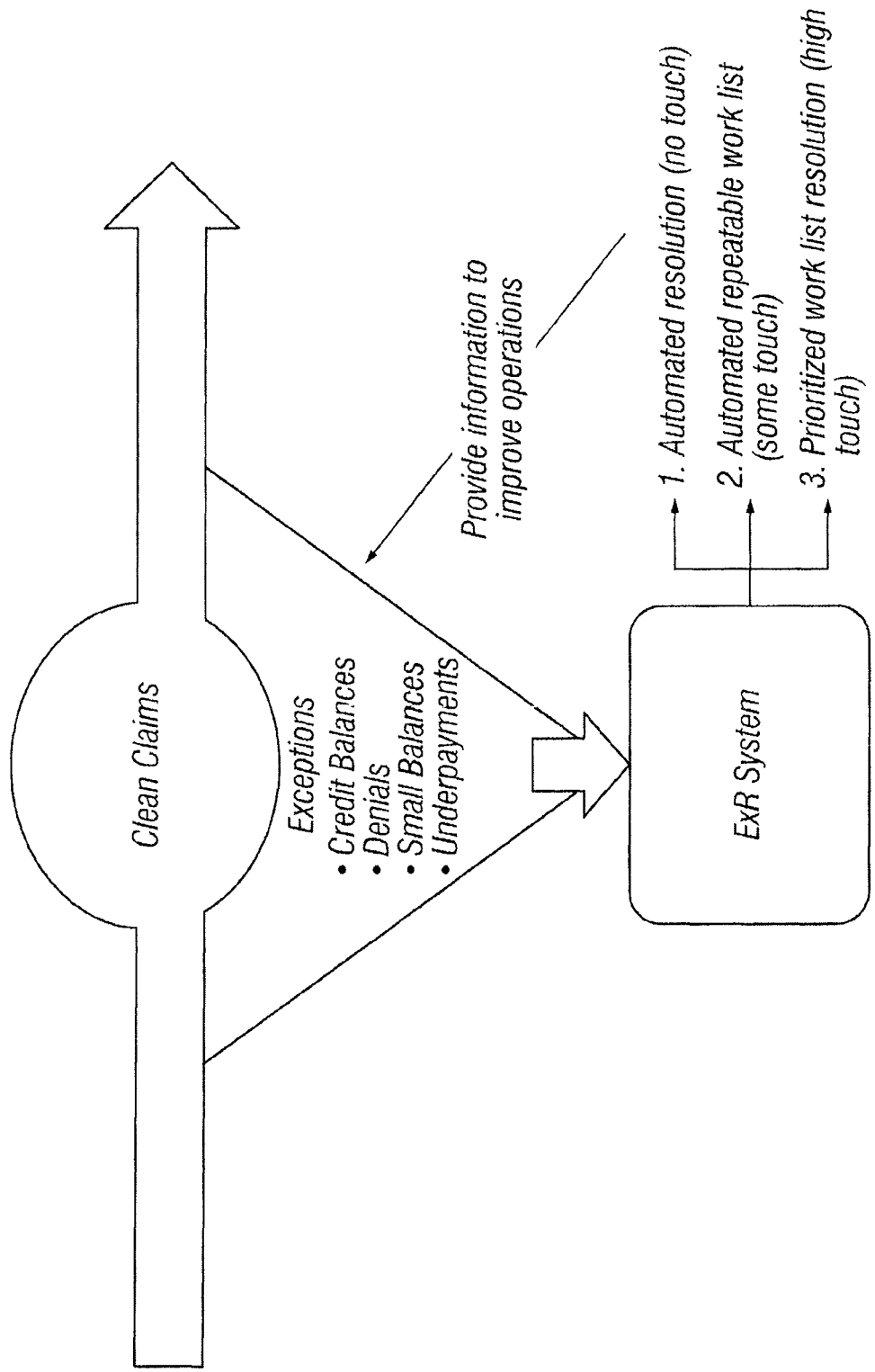
FIG. 3 is a diagraph illustrating an ExR system according to one embodiment.

FIG. 3 is a high level diagram of an example workflow involving the ExR system 206. In this example, there are transactions that result in "clean claims" in which no further work must be performed. In many health facilities, the vast majority of transactions result in clean claims; often, the clean claims amount of 85% of the transactions. However, there are account exceptions that must be dealt with by these facilities. By way of example, these exceptions could include, but are not limited to, bad debt, credit balances, denials, small balances and/or underpayments. These exceptions may be fed to the ExR system 206, which can make predictions on a recommended resolution. In the example shown, the ExR system 206 makes predictions that allow categorization between accounts in which an automated resolution is recommend, those in which an automated repeatable work list could be provided and those with a prioritized work list resolution.

Figure 4:
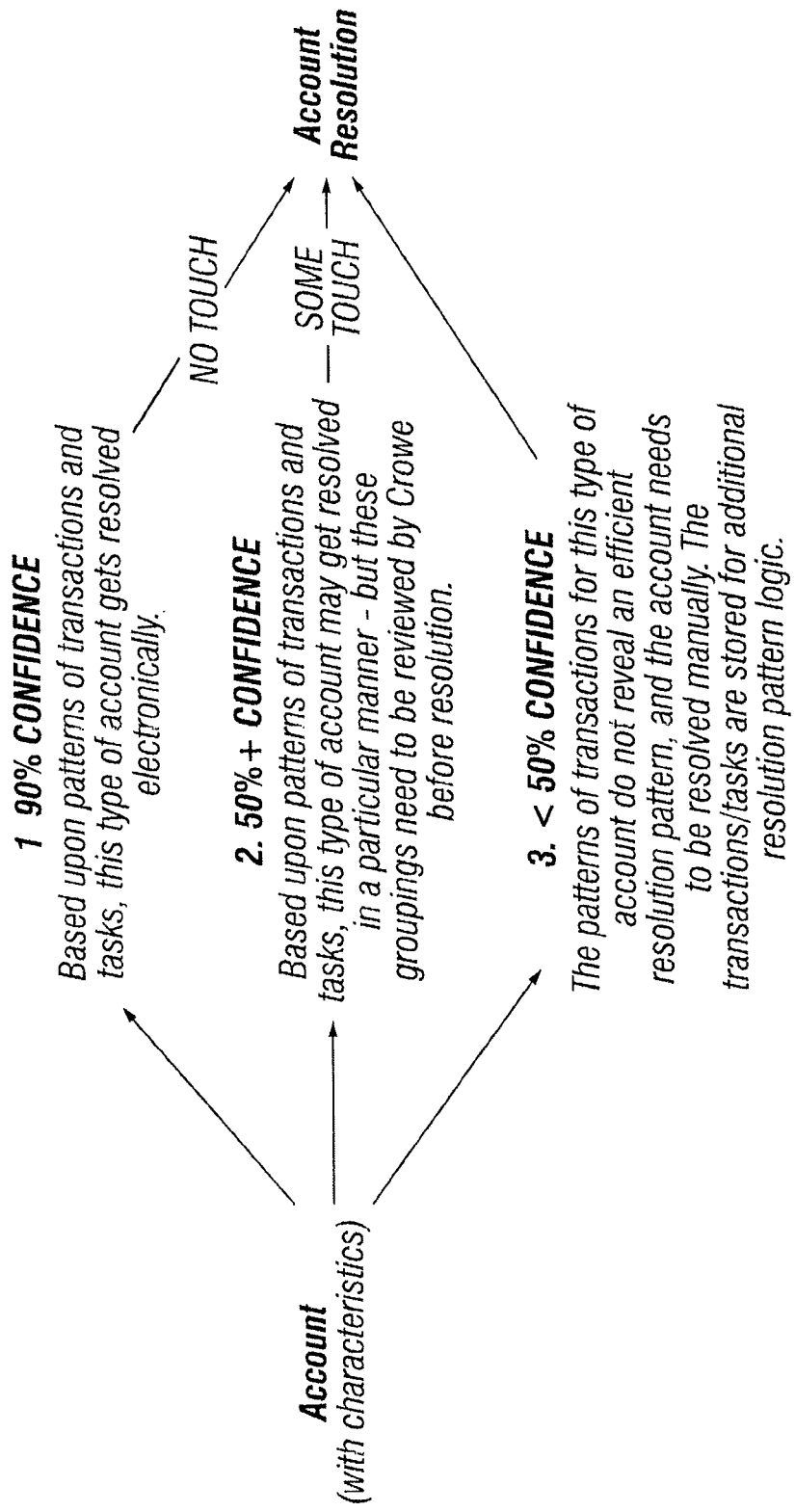
FIG. 4 is a diagram showing possible prediction confidence levels made by the ExR system according to one embodiment.

FIG. 4 illustratively shows potential predictions that may be made by the ExR system 206. In this example, if the ExR system 206 has a 90% confidence level that an account can be resolved electronically based on pattern recognition in the transactions, this account can be resolved without human interaction. Continuing with the example, a greater than 50% confidence level by the ExR system 206 that an account can get resolved in a particular manner based on patterns in the transactions, the ExR system 206 flags the account as needing to be reviewed before resolution with potentially a worklist or suggested resolution. For those accounts in which the ExR system 206 has less than 50% confidence of an efficient resolution based on the transaction patterns, the ExR system 206 flags the transactions as needing additional attention for resolution. One skilled in the art should appreciate that the confidence levels for which recommended predictions are made could be adjusted depending on the circumstances.

Figure 5:
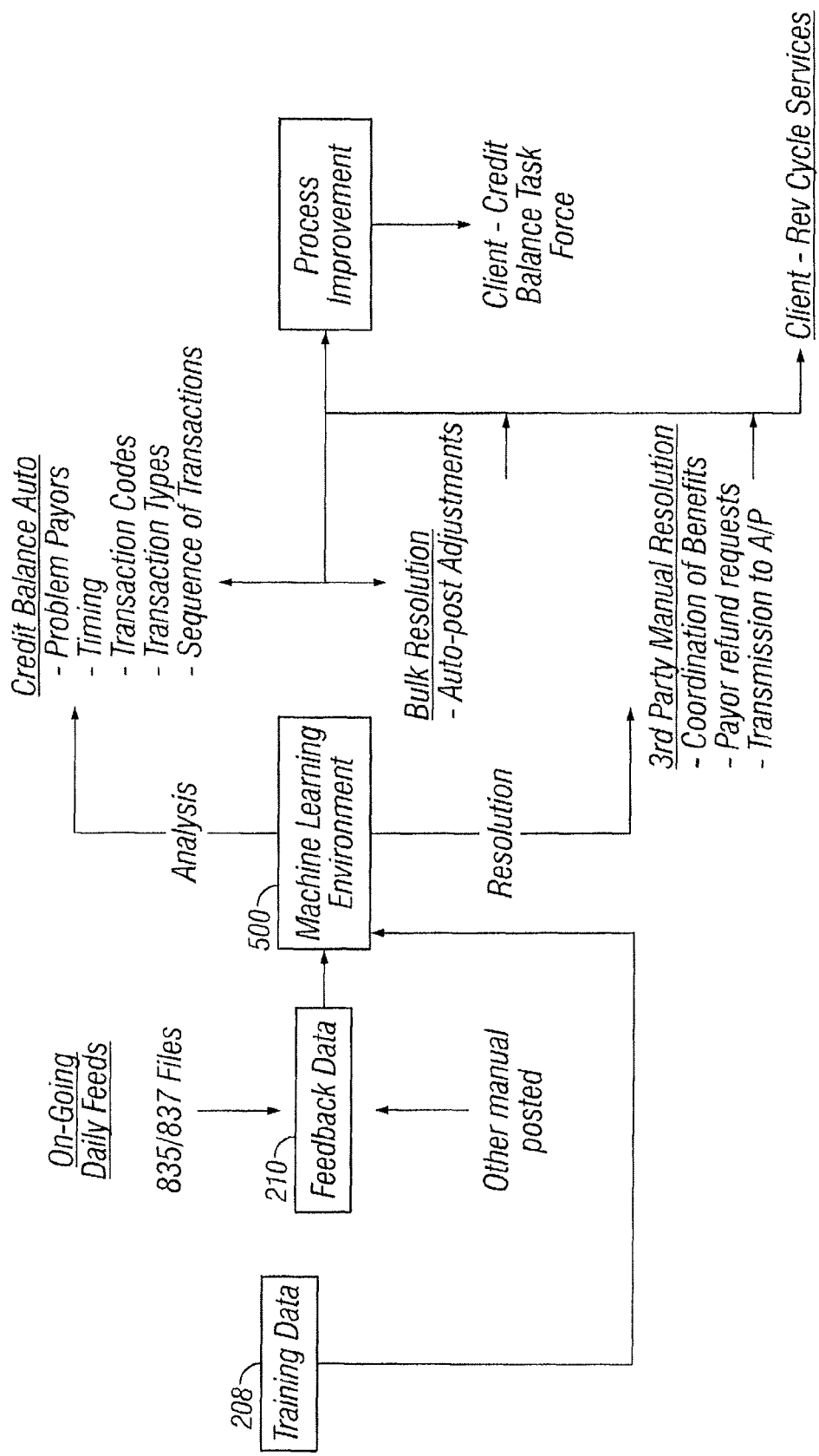
FIG. 5 is a simplified flow chart showing example operations of the ExR system according to one embodiment with credit balance open accounts.
Figure 6:
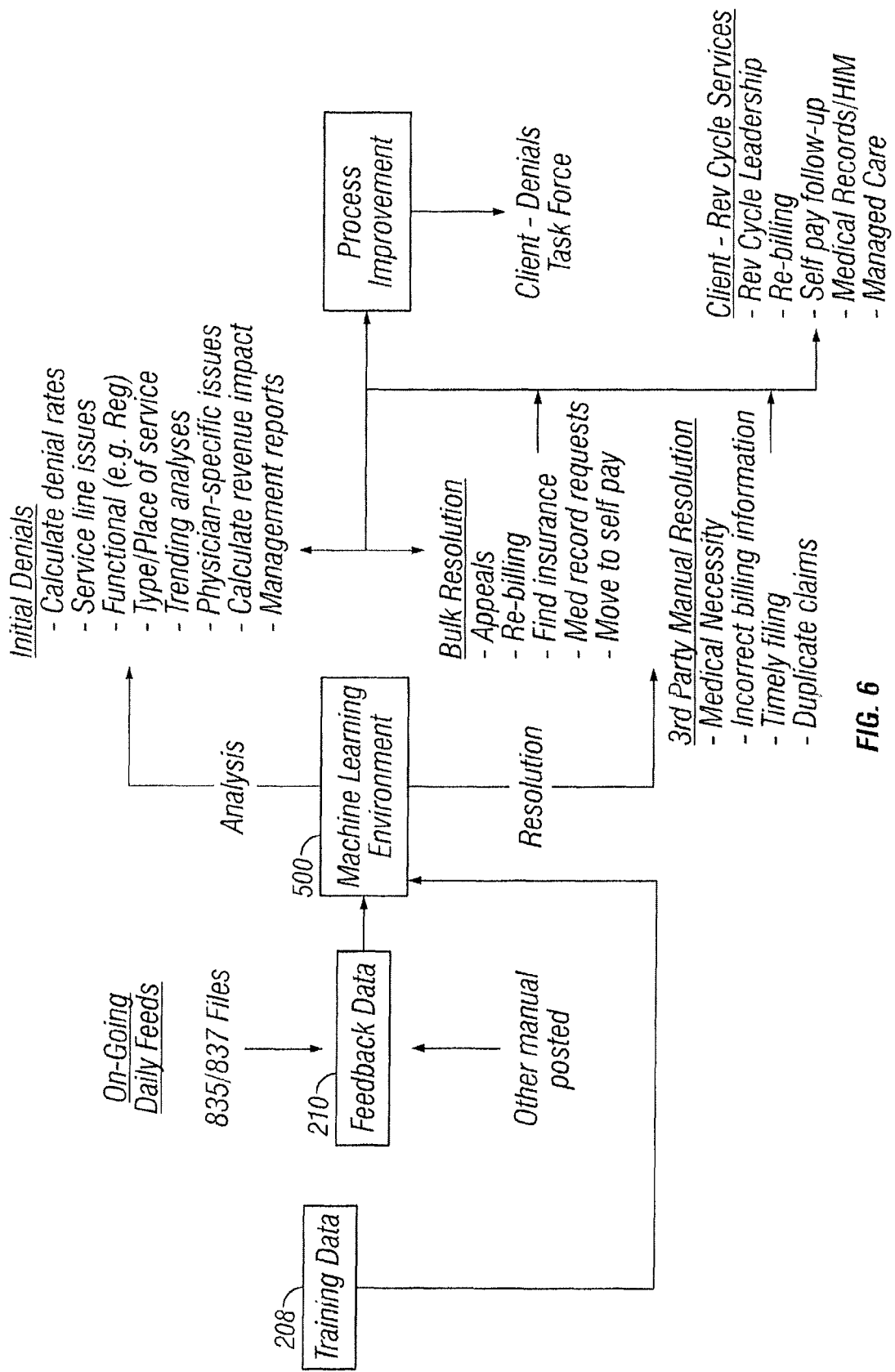
FIG. 6 is a simplified flow chart showing example operations of the ExR system according to one embodiment with initial denial open accounts.

FIGS. 5 and 6 illustrate the use of the ExR system 206 to resolve various accounts. In the example shown, the ExR system 206 includes a machine learning environment ("ML") 500 that utilizes historic patterns of transactions/tasks from the training data 208 and current transactional data 210 to determine the most efficient process to successfully resolve accounts. The example in FIG. 5 shows the use of the ML 500 to help resolve credit balances. In FIG. 6, the example shows the ML 500 operating to aid in resolving denial of benefits, such as involving insurance coverage and/or governmental benefits.

Figures 7, 8:
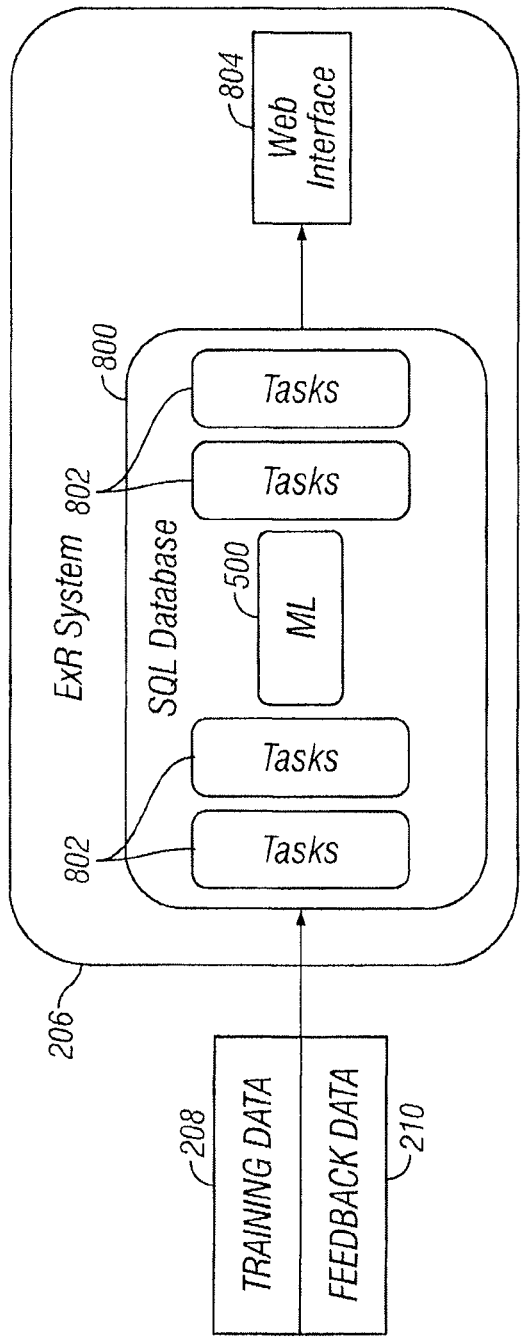

Referring to FIG. 7, the ML 500 sits at the center of the ExR system 206 and includes multiple models or sections, such as Credits, Denials, Bad Debt, etc. for predicting resolution actions. In the example shown, the feedback data 210 comes in on a regular basis (e.g., daily, monthly, etc.) and is processed through a Structured Query Language (SQL) database 800 for theming, calculations, reporting, and numerous additional tasks 802. At one point in the process, a call to the ML 500 is made from the database 800, which reads in a specific set of the new data, makes predictions, and outputs its prediction results back to the database 800. Additional tasks then take these prediction results, match them back to specific accounts, isolate actions and amounts, and make this available for a web interface 804 to interactively view.

Preprocessing

In general, preprocessing is done to get the data 208, 210 from how it comes in to the ML 500, to a format needed for modeling and predictions. The data is generally Type 2 in nature, meaning that for a given account, there will be a transaction history. For modeling and prediction purposes, there are goals for predicting the resolution pathway, which depends on the history of the account. However, the data needs to be transformed into Type 1 to ensure correct learning and predicting once per account. While the specifics of this depend on the overall goals for each ML model (e.g., Credits/Denials/Bad Debt/etc.), the general idea stays the same for this application. An account is in one state (e.g., credit balance) that matches a time when the ML 500 would make a prediction, then some type of action happens that resolves that specific account. Rules and algorithms then pick out this resolving transaction, identifying it as an "answer" to that given account. For the continuous feed of data coming in through the feedback data 210, the preprocessing would then filter out accounts that are in that state that need a prediction, and make those available to the ML model. Each specific ML section also has a set of features that describe an account. The specific set used for the Credits section is likely different from the Denials section, along with all others.

FIGS. 8-11 illustrate example steps performed for preprocessing for the credit section of the ML 500. This example is a type of account that could be passed on to the ML Credit model since it is in a credit state with a $19.34 credit balance. This type of account is deemed part of the test dataset. FIG. 8 has a column on the far right where the additional features would go that describe the account, but are left out here for purposes of simplicity. To train the model, accounts are needed that are in a state similar to that shown in FIG. 8, but are then later resolved. An example of this is shown in FIG. 9. This account from FIG. 9 was in a credit state, had a refund issued, and then became a zero balance account. The preprocessing would identify this last transaction as one that resolved the account. The data for this account can then be converted to a Type 1 format with a single row defining the history of the account (columns), and the last column the resolution, or "answer" to this account, as shown in FIG. 10. This data, as part of the training dataset 208, is now in a format to be able to train the ML model and make predictions when there is not resolving transactions, as shown in FIG. 11.

Overall Structure

Figure 12:
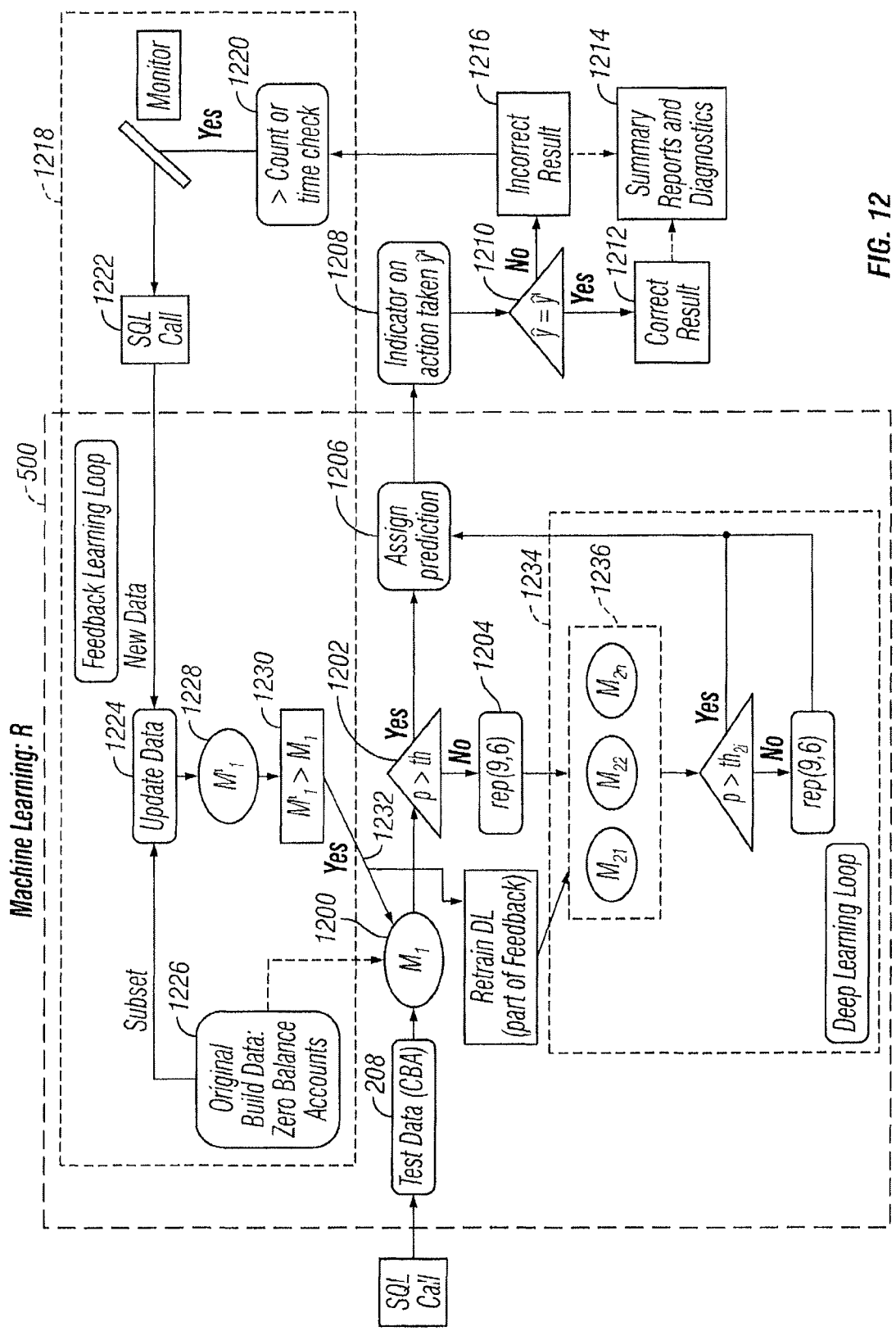
FIG. 12 is a simplified flow chart showing example operations of the machine learning environment according to one embodiment.

FIG. 12 shows the process flow of the ML 500 according to one embodiment, along with various boundaries, borders, and interfaces that are fully explained in subsequent sections.

Main Process Flow

From a high level perspective, once the original model, $M_1$ 1200, is built, new data comes in from the continuous data feed, are run through the preprocessing section, predicted against, and assigned the predicted category if their prediction probability, p, is above a client-specified threshold, th. The prediction is then passed back to the database 800 for subsequent tasks and shown to the user through the web interface 804 (FIG. 8). If the prediction probability is lower than the client-specified prediction threshold (Block 1202), a low confidence indicator is assigned to the account, which is denoted by rep(9,6) (Block 1204) in FIG. 12 (code for 999999). This enables a filtering process to take place so that additional attention can be given to review these specific accounts instead of automatically resolving them with the model prediction. The output passed back into the database 800 for the given account is the low confidence indicator, the original predicted resolution, and the probability of the original predicted resolution. More details on these terms are discussed below with respect to Deep Learning.

If their prediction probability, ρ, is above a client-specified threshold, th, (Block 1202), the ML 500 assigns a prediction to the transaction (Block 1206). The predicted outcome, ŷ (Block 1208), is then compared against the human decision on the account, ŷ' (Block 1210), and the database 800 stores the actions taken on that account. If the action taken is the same as the predicted result, the account would be identified as having a correct prediction (Block 1212). Summary reports and diagnostics are generated automatically for investigating model performance overall and within prediction classes. (Block 1214). The accounts having incorrect predictions (Block 1216) are then sent to a "holding" area, which will be used for Feedback Learning to improve the model performance.

Feedback Learning

As mentioned previously, when the human made a different decision for a particular account (Block 1216), an indicator is set so the specific account can be used for feedback learning to improve the model performance. There is a general need for this process, not only because models are based off of changing historical data and balancing posterior probabilities with frequencies that trends appear in the data and thus have inherent error, but also because of the nature on how the data feed is converted into something that can be modeled against. Going back to the Preprocessing Section, the resolutions to each account that are used to train the model are calculated by defined rules and algorithms. The case shown in that section is very simple and there is not a chance for error, but that is generally not the case with the data coming in on these accounts. Instead, it is common to see bouncing account balances (debit→zero→credit→debit→zero), duplicate transactions, offsetting/reversing transactions, etc. This makes the selection of the resolution transactions likely to have errors. Also, hospital administrators handling the accounts do not have a 100% accuracy either, which will then flow into the model.

The goal of the feedback learning process is to remove these accounts that are likely incorrect from the training data used to build the model, and add in the new accounts from the "holding" area that the model predicted a different outcome from the human decision. From the Incorrect Result box (Block 1216), these particular accounts are sent into the "holding" area in the Feedback Learning Loop, defined by dotted line 1218. Once there are enough accounts in the "holding" area, or a specific time threshold has passed (e.g., weekly, monthly, etc.) (Block 1220), there is a call from the database application (Block 1222) to initialize the feedback process.

The feedback process starts with getting the correct data set that will be used for retraining the model, M1, as defined by the Update Data box (Block 1224). The original training data 208 is randomly sampled to determine which observations are used in each iteration of the new model tests (Block 1226). For example, the matrix in FIG. 13 shows that observation 3 would not be used in the first iteration, observation 2 would not be used in the second iteration, etc. Then, all of the data from the "holding" area is added to the data used for each iteration, and makes up the Update Data box (Block 1224) for iteration i. The percentage of the original dataset sampled to be used as part of the Update Data depends on the respective sizes of both data sets (original and new), and is calculated to optimize data size stability (can grow and shrink slowly, as needed), according to the equation below.

$$n_{prop} = \begin{cases} 0.85 & \text{for } n_{new} \geq 0.1 * n_{orig} \\ 1 - \left(0.95 * \left(\frac{n_{new}}{n_{orig}}\right)\right) & \text{for } n_{new} < 0.1 * n_{orig} \end{cases}$$

$n_{new}$ = Observations of New Data (from "holding" area)

$n_{orig}$ = Observations of Original Build Data $n_{prop}$ = Proportions to sample from Original Build Data For each iteration, the update data (Block 1224) is used to create a new model M'1 (Block 1228) and judge the performance of the new model with model, M1 (Block 1230). At the end of each iteration, a score is calculated to determine if the new model is better than the old. In some embodiments, this score uses statistics from how the model performs against the validation data set, or a random 25% sample of the training data set used from the Update Data box for each iteration. Typically, the 25% used in the validation data set act as "hold-out" observations and are not used in the training of the model, for reasons of statistical stability, over-fitting, bias versus variance, etc. An example of the scores are shown at the bottom of the table in FIG. 13. These values are calculated from a supervised machine learning model of a logistic regression form, shown by the equation below, where the δ indicates the change in the statistic from the original model:

$$\text{logit}\left(\frac{\hat{s}_i}{1-\hat{s}_i}\right) = \sum_j W_j \beta_j X_{ij} \quad X_j \in (\delta_{APER}, \delta_{FPR}, \delta_{percT})$$

$$\hat{s}_i = \frac{e^{(\beta_0 + W_1\beta_1\delta_{APER} + W_2\beta_2\delta_{FPR} + W_3\beta_3\delta_{percT})}}{1 + e^{(\beta_0 + W_1\beta_1\delta_{APER} + W_2\beta_2\delta_{FPR} + W_3\beta_3\delta_{percT})}}$$

In addition, there is a weight parameter, W, that allows individual clients to specify if a certain increase in performance based on one statistic means more to them than others. For example, one client might say a 0.01% decrease in model accuracy is acceptable if there is an increase of 5% of the accounts that can then be automated. Other clients might be comfortable with a 0.1% decrease in accuracy to get 5% more automated.

After all iterations have been complete, either defined by a maximum number (e.g., 10), or a maximum time allowed (e.g., 20 minutes), the dataset used in the iteration that had the maximum score is then used to retrain the model. This is done because the model object is not saved during the iteration and score process, due to memory constraints with model sizes. The score should generally be above 0.50 in terms of a logistic regression output to say that the new model ($M_1'$) is better than the original ($M_1$) model, but if the statistics used to calculate the model performance all move in the correct direction, and the score is less than 0.50, the model is still said to be better and will be retrained with that data set.

The new model is then saved as M1, (as indicated by arrow 1232) and will be used the next time predictions are needed through the Main Process Flow. For backup purposes, the model history could be kept. Below is a set of instructions illustratively showing the feedback learning process according to an embodiment of this disclosure.

Pseudo Code: Feedback Learning
1. Load original $M_1$ model performance statistics
2. Calculate proportion of original data to sample
3. Create sampling matrix
4. for iteration i=1 until max iteration or max time limit
   a. Combine sample data from matrix column i with new data
   b. Divide into training (75%) and validation (25%) data sets
   c. Train model with training data set
   d. Test performance against validation data set
   e. Get error statistics of model (APER, FPR, percT, etc.)
   f. Calculate and store score based on error statistics
   g. Store iteration time for breakout
5. end for
6. if max(scoresVector)>0.5 or AND(all δ(APER, FPR, percT) are in better direction then
   a. Get index for data set to be used
   b. Combine sample data from matrix column i with new data
   c. Divide into training (75%) and validation (25%) data sets
   d. Train model with training data set
   e. Test performance against validation data set
   f. Get error statistics of model (APER, FPR, percT, etc.)
   g. Save model object as $M_1$
   h. Save model performance statistics for next feedback learning
7. end if
8. Store model performance statistics in log file Deep Learning Since the ML model is programmed to only assign a prediction when the confidence level is above a certain client-defined threshold, not all of the data will have a predicted resolution assigned to it. This can be a drawback if there is a substantial amount of data that falls into this category, indicating that more human interaction is needed with the data instead of automation. Deep Learning comes in as a separate loop in the overall ML 500, indicated by dotted line 1234, which can improve upon this issue.

During the development of the M1 model, if it is discovered that a large proportion of the data is predicted at a low confidence, and thus marked with the low-confidence indicator (Block 1202), it may be necessary to create additional models in order to increase the total amount of data that has a prediction assigned. For the notation in FIG. 12, the models are still designated by an oval with an M inside (Block 1236). In the embodiment shown, the first sub-digit after the M still indicates the level of the model, and the second sub-digit indicates the model number. The main process flow only has the $M_1$ model, where the 1 indicates the first level. Inside the deep learning loop, three ovals are shown at the second level, as shown with the first sub-digit, M2, for purposes of example. There can be any number of models on the second level, as well as any number of subsequent levels, just coming at the cost of added complexity and development time.

In general, any model in the second level uses some feature set as the explanatory variables, along with some output created from the level above. Models in the third level would be use outputs from the second level, and so on. Each model can be as complex as the original $M_1$ model, or very simple. One example of a simple level-two model could be a case where M1 predicts classification B much better than all other classifications. Error distributions might show that the overall prediction threshold, th, should be set to roughly 90% (below which would get low confidence indicators). But since B is predicted much better, maybe M1 does not predict B incorrect until the confidence is around 60%. A simple M21 model could be: if the original prediction was B, assign the prediction (instead of the low confidence indicator) as long as the prediction probability is above 60%. On the other side, each M2, model can each be its own neural network, but with slightly different input conditions, variables available, or output conditions used from the $M_1$ model. For levels three to n, notation follows:

$$M_{ijk} \text{ where } \begin{cases} i & \text{level} \\ j & \text{number of previous stage} \\ k & \text{model number} \end{cases}$$

So $M_{321}$ would indicate a model in the third level, which uses input from the $M_{22}$ model. $M_{332}$ would indicate a third level model, using input from M23, and it is the second model in that level that traces to $M_{23}$. When there are deep learning models, the feedback process not only attempts to retrain the $M_1$ model, but also will then attempt to retrain subsequent levels if successful, since the output of the higher stage model acts as an input to the lower stages. If $M_1$ is retrained successfully (a better performing model is found), all level two models will be attempted to be retrained. If there are two, level-two models $M_{21}$ and $M_{22}$, and both one model at a deeper stage $M_{311}$ (from $M_{21}$) and $M_{322}$ (from $M_{22}$), $M_{311}$ will only be attempted to be retrained if $M_{21}$ is retrained successfully. This process continues automatically for all levels until nothing else has to be retrained.

Example Models Used

The specific models used for $M_1$ in the main process flow, along with any used in the deep learning loops, depend on the original build data for the particular project. While the problem is a semi-supervised in nature (due to the response variable being calculated in the preprocessing step), the models responsible for making the predictions at a given probability, are of the supervised type, including (but not limited to), random forests, support vector machines, neural networks, extremely randomized trees, etc., and all of their respective variants. The main focus on the importance and uniqueness of the ML 500 within the ExR system 206 is not the specific model derivations themselves, but how they are able to be used as a full system with the nature of this data and with the ability for automatic feedback learning.

Threshold Predictions

From an application level requirement, actions are only meant to be automated when the ML 500 is highly confident in the recommended action. For this reason, the models used must be able to result in some type of probability measurement of a given prediction. While all models define and calculate this differently, the following example explains that for the probability calculation from the output of the random forest algorithm.

At a high level, a random forest is a set of decision trees that are different from each other. After the model is trained, a new observation is predicted against by going through each decision tree to get a resulting predicted classification. The counts for each classification are totaled for that given observation, and divided by the total number of trees. Each decision tree likely will not have the same predicted outcome, which is one of the points of the derivation of the random forest algorithm. Consider an example of a model with 10 trees and four possible outcomes (A, B, C, D). For the first object that was predicted against, six trees resulted in an A classification, three resulted in a B classification, and one in a D classification. The respective probabilities for these predictions would then be 60%, 30%, 0%, and 10%. This would act as the output to the model. The ML 500 would then only keep the highest predicted percentage and classification, resulting in a prediction of classification A at 60% for the above example. Determining if this prediction should be reassigned to the low confidence indicator and sent into the deep learning loop depends on the tuning of the specific model and prediction threshold.

Prediction Threshold

Figure 14:
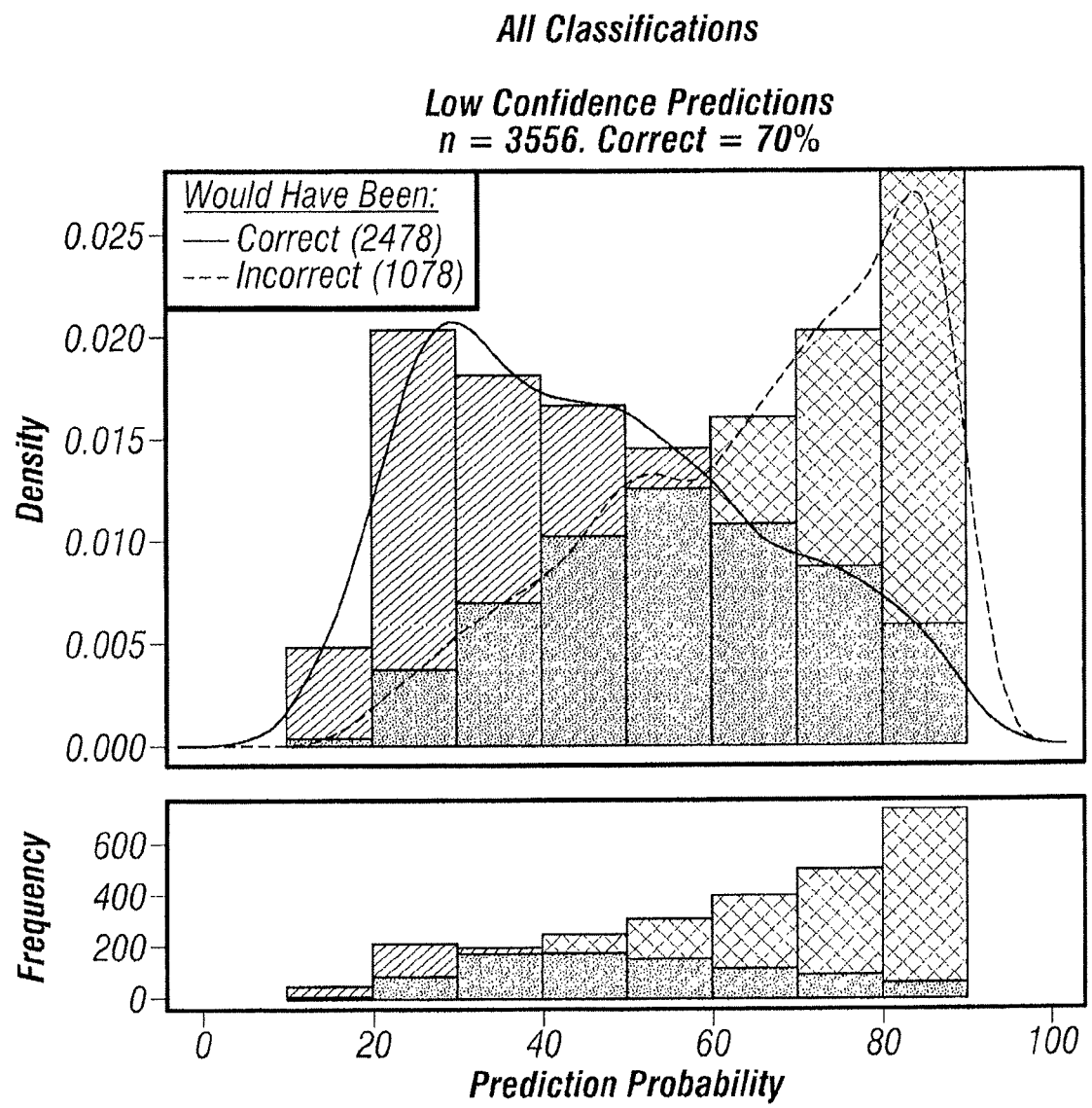
FIGS. 14 and 15 are graphs illustrating optimization of models used by the machine learning environment according to one embodiment.
Figure 15:
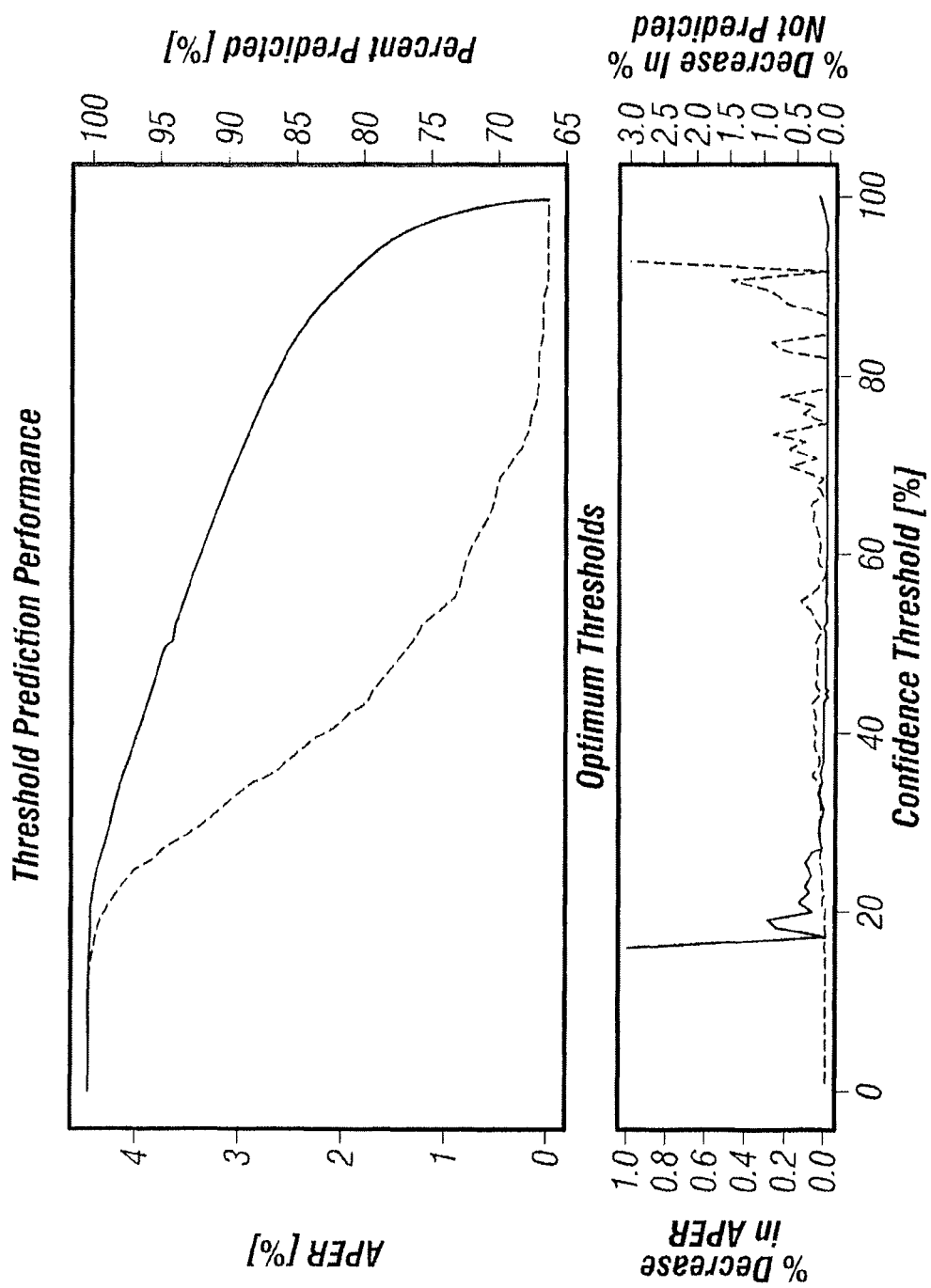

The prediction threshold depends not only on the model performance statistics, but also the client preferences, and the ML 500 is built for both purposes. During the initial training of the model, plots like that of FIGS. 14 and 15 are created and studied to recommend the optimal threshold that minimizes the overall error, maximizes the amount of data predicting against (percentage falling above the prediction threshold so a low confidence indicator will not be assigned), and balancing additional statistics and measures for the overall data set, and within each classification. These plots are also created and studied for potential deep learning models. Some of the additional statistics for each classification group, i, include:

$$\text{Sensitivity}_i = \frac{(\text{Predicted Correct})_i}{(N \text{ Actual})_i}$$

$$FPR'_i = \frac{(\text{Predicted Wrong})_i}{(N \text{ Actual})_i}$$

$$FNR_i = \frac{\text{Missed Prediction}}{(N \text{ Actual})_i}$$

$$FDR_i = \frac{(\text{Predicted Wrong})_i}{(N \text{ Predicted})_i}$$

Main Process Flow Output

The dotted box 500 of FIG. 12 shows the boundary of what is created from the ML process and what is considered an output to pass back in to the database 800. In some embodiments, the output is a Comma Separated Value (CSV) file with an AccountID, Prediction, Prediction Probability, and the Original Prediction. The AccountID is a secured value that is generated within the database system that can be looked up to match with the patient Account Number. The numbers are different for security purposes, and can only be matched back up in the database. The Original Prediction gives the predicted value as if there was not a low-confidence indicator. FIG. 16 below shows this sample output, with the low confidence indicator (999999) showing up in the last row because the confidence threshold was set to 90%, and the prediction probability was below that value. The original prediction, however, was a category of 3. The database then picks up this table, matches AccountID back to Account Number, and places the three result columns into the table from which the web interface 804 pulls data.

Although the present disclosure has been described with reference to particular means, materials, and embodiments, from the foregoing description, one skilled in the art can easily ascertain the essential characteristics of the invention and various changes and modifications may be made to adapt the various uses and characteristics without departing from the spirit and scope of the invention.

What is claimed is:

1. One or more non-transitory, computer-readable storage media comprising a plurality of instructions stored thereon that, in response to being executed, cause a computing device to:
create a plurality of machine learning models comprising at least a credit model and a denial model for predicting resolutions to open accounts by:
obtaining training data representative of historical account transactions between a plurality of patients and a healthcare facility, wherein at least a portion of the training data is targeted specifically for each of the credit model and the denial model;
analyzing the training data to create the plurality of machine learning models configured to make predictions representative of resolutions of open account transactions, wherein the credit model and the denial model are configured to make predictions based on respective open account types of credit balances in which the credit model is to predict an automated resolution based on identifying one or more of problem payors, timing issues, transaction code issues, transaction type issues, or transaction sequence issues and denial of benefits in which the denial model is to predict an automated resolution based on identifying one or more of denial rates, service line issues, healthcare provider specific issues, revenue impact, or management reports, wherein the open account transactions are transactions for accounts that have previously been billed and remain unpaid;
training and/or retraining at least a portion of the plurality of machine learning models by making predictions regarding open account transactions,
wherein in response to at least one of the plurality of machine learning models making a prediction at a confidence level exceeding a threshold confidence level regarding an open account transaction: (i) assigning the prediction to the open account transaction; (ii) flagging the prediction for a holding area when the prediction is a different outcome from a human decision for the open account transaction; and (iii) periodically retraining the plurality of machine learning models based on open account transactions associated with the holding area;

wherein in response to the confidence level associated with the prediction being less than the threshold confidence level regarding the open account transaction, performing a deep learning process by (i) making predictions regarding the open account transaction with a plurality of different machine learning models that are different levels to each other in that a machine learning model of a subsequent level includes output from a machine learning model of a previous level; and (ii) retraining the machine learning model that made the prediction based on the deep learning process;

applying the machine learning model to predict resolutions of a plurality of open account transactions as a function of open account type by:

making predictions on a level of human interaction needed to resolve the plurality of open account transactions using the plurality of machine learning models; and electronically resolving at least a portion of the open accounts based on predictions made by the plurality of machine learning models.

2. The non-transitory, computer-readable storage media of claim 1, wherein at least a portion of the plurality of machine learning models are configured to categorize at least a portion of the open account transactions into a category of at least two categories based on a level of human interaction needed to resolve each respective open account transaction.

3. The non-transitory, computer-readable storage media of claim 2, wherein at least a portion of the plurality of machine learning models are configured to categorize at least a portion of the open account transactions into: (1) a first category if an exception can be resolved by an automated solution without any human involvement, (2) a second category if an exception can be resolved by an automated repeatable work list with some human involvement, and (3) a third category if an exception needs to be resolved with a higher degree of human involvement.

4. The non-transitory, computer-readable storage media of claim 3, wherein at least a portion of the plurality of machine learning models are configured to categorize into the first, second and third categories based on a predicted confidence level on an amount of human involvement needed to resolve an exception.

5. The non-transitory, computer-readable storage media of claim 4, wherein at least a portion of the plurality of machine learning models are configured to categorize into the first category if the predicted confidence level is above a first threshold confidence level, categorize into the second category if the predicted confidence level is above a second threshold confidence level, categorize into the third category if the predicted confidence level is above a third threshold confidence level.

6. The non-transitory, computer-readable storage media of claim 5, wherein the third threshold confidence level is less than the first threshold confidence level and the second threshold confidence level, wherein the second threshold confidence level is less than the first threshold confidence level.

7. The non-transitory, computer-readable storage media of claim 4, wherein at least a portion of the plurality of machine learning models are configured to categorize an exception in the first category if the predicted confidence level is above ninety percent.

8. The non-transitory, computer-readable storage media of claim 4, wherein at least a portion of the plurality of machine learning models is configured to categorize an exception in the second category if the predicted confidence level is less than ninety percent, but above fifty percent.

9. The non-transitory, computer-readable storage media of claim 4, wherein at least a portion of the plurality of machine learning models are configured to categorize an exception in the third category if the predicted confidence level is less than fifty percent.

10. The non-transitory, computer-readable storage media of claim 9, wherein at least a portion of the plurality of machine learning models are configured to flag any exceptions categorized in the third category for a holding area for additional attention for resolution.

11. The non-transitory, computer-readable storage media of claim 10, wherein at least a portion of the plurality of machine learning models are periodically updated by obtaining current transactional data and analyzing both the training data and the current transactional data to update the plurality of machine learning models on how to make predictions representative of resolutions of open account transactions.

12. The non-transitory, computer-readable storage media of claim 10, wherein at least a portion of the plurality of machine learning models are periodically updated with at least a portion of the transactions in the holding area for which the machine plurality of learning models predicted a different outcome from a human decision.

13. The non-transitory, computer-readable storage media of claim 12, wherein at least a portion of the plurality of machine learning models is periodically updated with the portion of the transactions in the holding area for which the plurality of machine learning models predicted a different outcome from a human decision and a sample of the training to update the plurality of machine learning models on how to make predictions representative of resolutions of open account transactions.

14. The non-transitory, computer-readable storage media of claim 13, wherein upon creating an updated machine learning model based on the transactions from the holding area and sample of training data, a comparison is made whether the updated machine learning model makes more accurate predictions on resolutions of open account transactions than an existing machine learning model.

15. The non-transitory, computer-readable storage media of claim 14, wherein if the updated machine learning model is determined to make more accurate predictions on resolutions of open account transactions than the existing machine learning model, the updated machine learning model replaces the existing machine learning model.

16. The non-transitory, computer-readable storage media of claim 14, wherein a determination of whether the updated machine learning model makes more accurate predictions than the existing machine learning model is based on a score from how each respective machine learning model performs against a validation data set.

17. The non-transitory, computer-readable storage media of claim 16, wherein the scoring of how the respective machine learning models performs includes a weight for determining performance based on one or more of a maximum time allowed for the machine learning model to analyze the validation data set and/or an accuracy of predicting resolutions of open account transactions.

* * * * *